United States Patent [19]

Wu

[11] Patent Number: 5,976,823
[45] Date of Patent: Nov. 2, 1999

[54] LOW RANGE TOTAL AVAILABLE CHLORINE TEST STRIP

[75] Inventor: Wen H. Wu, Elkhart, Ind.

[73] Assignee: Integrated Biomedical Technology, Inc., Elkhart, Ind.

[21] Appl. No.: 09/256,001

[22] Filed: Feb. 23, 1999

Related U.S. Application Data

[63] Continuation-in-part of application No. 09/025,676, Feb. 18, 1998, Pat. No. 5,888,758, which is a continuation-in-part of application No. 08/822,570, Mar. 19, 1997, Pat. No. 5,811,254.

[51] Int. Cl.$^6$ ............................... C12Q 1/28; C12Q 1/00
[52] U.S. Cl. .......................... 435/28; 435/4; 435/283.1; 436/63
[58] Field of Search ............................... 435/28, 4, 283.1; 436/63

[56] References Cited

U.S. PATENT DOCUMENTS

| | | | |
|---|---|---|---|
| 3,718,605 | 2/1973 | Storm | 252/408 |
| 4,049,382 | 9/1977 | Ross, Jr. et al. | 23/230 R |
| 4,071,317 | 1/1978 | Lam | 23/253 TP |
| 4,071,318 | 1/1978 | Lam | 23/253 TP |
| 4,071,321 | 1/1978 | Lam | 23/253 TP |
| 4,092,115 | 5/1978 | Rupe et al. | 23/230 R |
| 4,290,773 | 9/1981 | Magers et al. | 23/230 B |
| 4,318,984 | 3/1982 | Magers et al. | 435/14 |
| 4,339,242 | 7/1982 | Magers et al. | 23/230 B |
| 4,339,243 | 7/1982 | Magers et al. | 23/230 B |
| 4,340,392 | 7/1982 | Magers et al. | 23/230 B |
| 4,340,393 | 7/1982 | Magers et al. | 23/230 B |
| 4,340,394 | 7/1982 | Magers et al. | 23/230 B |
| 4,340,395 | 7/1982 | Magers et al. | 23/230 B |
| 4,380,585 | 4/1983 | Magers et al. | 436/66 |
| 4,904,605 | 2/1990 | O'Brien et al. | 436/169 |
| 4,938,926 | 7/1990 | Reiss | 422/58 |
| 5,300,442 | 4/1994 | Frant | 436/125 |
| 5,362,650 | 11/1994 | Harp | 436/125 |
| 5,491,094 | 2/1996 | Ramana et al. | 436/125 |
| 5,811,254 | 9/1998 | Wu | 435/28 |
| 5,888,758 | 3/1999 | Wu | 435/28 |

OTHER PUBLICATIONS

Johnson et al., "Stabilized neutral orthotolidine, Snort, colorimetric method for chlorine," *Analytical Chemistry*, 41, No. 13, 1744–1750 (1969).

Bauer et al., "Use of syringaldazine in a photometric method for estimating 'free' chlorine in water," *Analytical Chemistry*, 43, No. 3, 421–425 (1971).

Holland et al., "A safer substitute for benzidine in the detection of blood," *Tetrahedron*, 30, 3299–3301 (1974).

Standefer et al., "Use of tetramethylbenzidine in plasma hemoglobin assay," *Clin. Chem.*, 24, 4, 749–751 (1977).

Liem et al., "Quantitative determination of hemoglobin and cytochemical staining for peroxidase using 3,3',5,5'-tetramethylbenzidine dihydrochloride, a safe substitute for benzidine," *Analytical Biochemistry*, 98, 388–389 (1979).

Liebermann, Jr. et al., "Development of the FACTS procedure for combined forms of chlorine and ozone in aqueous solutions," *American Chemical Society*, 14, No. 11, 1395–1400 (1980).

*Primary Examiner*—Louise N. Leary
*Attorney, Agent, or Firm*—Marshall, O'Toole, Gerstein, Murray & Borun

[57] ABSTRACT

A composition, method, and test device for determining a low concentration of total available chlorine concentration in a test sample are disclosed. The test device includes a test pad having a suitable carrier matrix incorporating an indicator reagent composition capable of converting combined available chlorine to free available chlorine and of interacting with free available chlorine to produce a detectable and measurable response for total available chlorine over a range of 0 to about 2 ppm total available chlorine in the test sample. An indicator reagent composition contains: (a) an indicator dye that is responsive to free available chlorine, such as tetramethylbenzidine, (b) a buffer, (c) an optional surfactant, (d) a catalyst, and (e) a polymer. An indicator reagent composition is incorporated into a carrier matrix, like filter paper, to provide a test pad useful in a dry phase total available chlorine assay of a test sample, such as a source water for a hemodialysis unit.

23 Claims, No Drawings

LOW RANGE TOTAL AVAILABLE CHLORINE TEST STRIP

CROSS-REFERENCE TO RELATED APPLICATIONS

This is a continuation-in-part application of U.S. application Ser. No. 09/025,676, filed Feb. 18, 1998, now U.S. Pat. No. 5,888,758, which is a continuation-in-part application of U.S. application Ser. No. 08/822,570, filed Mar. 19, 1997, now U.S. Pat. No. 5,811,254.

FIELD OF THE INVENTION

The present invention relates to a composition, method, and test device for determining the total available chlorine concentration of a test sample. More particularly, the present invention relates to a method and test device for assaying a liquid test sample, such as a sanitizing solution, for a low total available chlorine concentration of 0 to about 2 ppm total available chlorine by using an improved indicator reagent composition. The indicator reagent composition undergoes a detectable and measurable response upon contact with a test sample containing a low concentration of free available chlorine. Contrary to prior compositions and methods, the present method has the advantage of quantitatively measuring a low concentration of total available chorine.

BACKGROUND OF THE INVENTION

The use of chlorine as a sanitizer or disinfectant for various water supplies and various types of equipment, like food processing equipment and medical equipment, such as a hemodialysis unit, is common. Because the amount of available chlorine in an aqueous solution relates directly to the disinfecting or sanitizing activity of the solution, a test which rapidly and accurately measures available chlorine is important.

The available chlorine family is comprised of compounds which, when in aqueous solution, yield solutions of hypochlorous acid. The available chlorine family is further divided into compounds containing free available chlorine and compounds containing combined available chlorine. The sum of free available chlorine and combined available chlorine is termed total available chlorine.

Free available chlorine encompasses chlorine-containing compounds in aqueous solution such as hypochlorous acid, hypochlorite ion, and, in strong acid solutions, free chlorine. The use of free available chlorine as a disinfectant for water supplies and equipment is widespread because of its low cost, convenience, and effectiveness as an antiseptic agent in relatively low concentrations. For example, free available chlorine is used as a disinfectant in a majority of hemodialysis centers.

Combined available chlorine, also termed bound available chlorine, mainly encompasses organic chloramines, which release only a small amount of free available chlorine in aqueous solution. Chloramines are formed from chlorine reacting with amine compounds in water. The amine compounds can be an impurity in the water or arise from ammonia added to water with chlorine during water disinfection. Ammonia and chlorine are added to the water to form chloramines which stabilize chlorine from decomposition and/or evaporation, and also increases the bacteriocidal potency of chlorine. Depending on the ratio of chlorine-to-ammonia and the acidity of the water, chloramines formed from chlorine and ammonia are a mixture of monochloramine, dichloramine, and trichloramine at various ratios. Although monochloramine is the main chloramine of concern due to its toxicity, removal of all chlorine is essential for safe and effective operation of a dialysis water purification system.

Conventionally, combined available chlorine has not been considered an effective disinfectant or sanitizer. Accordingly, prior chlorine assays have focused on assays for free available chlorine, i.e., the active disinfectant. For example, assays disclosed in Rupe et al. U.S. Pat. No. 4,092,115 and Ramana et al. U.S. Pat. No. 5,491,094, consider combined available chlorine as an interferant in the assay for free available chlorine, and the assays have been designed only to measure free available chlorine. However, in some applications, it is important to assay for total available chlorine.

For example, chlorine is used in hemodialysis centers to sanitize hemodialysis units because chlorine is an effective and economical sanitizing agent. It is important to clean and disinfect a hemodialysis unit between each dialysis session to prevent pathogen contamination from patient to patient. However, chlorine also is a very toxic compound that can cause hemolysis even when only a trace amount of chlorine diffuses from the hemodialysis unit into the blood of an individual. Therefore, if an assay for residual chlorine in a hemodialysis unit detects only free available chlorine, a potentially toxic amount of combined available chlorine, which slowly generates free available chlorine, can be present to adversely affect an individual subsequently connected to the hemodialysis unit. Trace amounts of free available chlorine also can adversely affect filtration membranes of the hemodialysis unit.

Combined available chlorine is considered highly toxic because of its electronic neutrality and ability to penetrate cell membranes. In a municipal source water, combined available chlorine always exists in various proportions relative to total available chlorine. Combined available chlorine is formed in a reaction of free available chlorine either with amine compounds, which are present as contaminants in the source water, or with ammonia, which is added to the water with free chlorine to stabilize the chlorine and to increase the bacteriocidal potency of the chlorine disinfectant.

With respect to a dialysis unit, all chlorine species in a water supply are removed before the water can be used in hemodialysis. Chlorine removal is usually performed by passing the water through a water purification tank containing activated carbon, and then through a reverse osmosis column. The presence of combined available chlorine in the water affects the efficacy of the carbon tank in removing all chlorine species. Knowledge of the concentration of total chlorine is important in designing the water purification system, as well as devising a method of monitoring chlorine in the purified water.

Occasionally, a trace amount of chlorine leaks through the tank. If the chlorine leaking through the tank is all, or substantially, combined chlorine, this suggests exhaustion of carbon tank capacity. However, if the chlorine leaking through the tank contains a high proportion of free chlorine, this indicates the presence of a mechanical defect, such as channelling through the activated carbon inside the tank or an insufficient contact time between the water and the activated carbon. Determination of both the free and combined available chlorine is important in managing the water purification for dialysis.

Therefore, when a sanitizing solution is used in medical or food processing equipment, two critical chlorine levels must be monitored. First, the free available chlorine concentration must be sufficiently high to perform a sanitizing or disinfecting function, i.e., at least about 1000 ppm (parts per million) free available chlorine is needed to effectively sanitize equipment. Typically, a chlorine concentration sufficient for equipment sanitization is about a 1 to 10 volume dilution of a 5.25% (by weight) sodium hypochlorite with water, to provide a solution containing about 0.5% to about 0.6% (by weight) sodium hypochlorite, i.e., about 5000 to about 6000 ppm chlorine. During the sanitizing process, the sanitizing solution is assayed periodically to ensure that sufficient free available chlorine is present to sanitize the equipment.

After the sanitizing function is completed, and before use, the equipment is rinsed with water to flush residual chlorine from the equipment. The rinse water also is assayed for available chlorine to ensure that the level of residual available chlorine is below the maximum allowable level, e.g., 0.5 ppm as recommended by the Association of Advancement of Medical Instrumentation (AAMI). In practice, the residual available chlorine concentration is essentially zero, or at least below the previous lowest detectable levels of about 0.1 to about 0.2 ppm, i.e., equivalent to a 1 to 100,000 water dilution of 5.25% (by weight) sodium hypochlorite.

A chlorine test strip having a broad range chlorine sensitivity of up to 5,000 ppm can be used to monitor the presence and absence of chlorine during the sanitizing and cleaning process. However, when assaying the water quality of a purified source water for use in a dialysis unit, a much more stringent water quality standard is used.

Municipal water normally contains 0.5 to 3.0 ppm chlorine in order to suppress the growth of microorganisms during the transport of water from the water treatment plant to consumers. Because free chlorine is not stable and quickly decomposes during water distribution, ammonia commonly is added with chlorine to generate chloramine. As previously stated, chloramine is less reactive than free chlorine, and is much more stable. Therefore, chloramine is a more effective disinfectant because of its long-lasting reactivity. For the same reason, chloramine also is considered a more toxic water contaminant, particularly when the water is to be used in hemodialysis units.

The Association for the Advancement of Medical Instrumentation (AAMI) standards rate water containing greater than 0.1 ppm of chloramine as unsafe for hemodialysis use. In almost all dialysis facilities, the tap (e.g., the source) water, therefore, is routinely filtered through a bed of activated carbon to remove any trace amount chlorine and/or chloramine. The effectiveness of the carbon tank is constantly monitored to ensure that the chlorine total/chloramine level is less than 0.1 ppm, and preferably zero. Because of the extremely low concentration of chlorine and, particularly, because of the slow reactivity of chloramine, no presently available test strip allows a convenient quantitative assay for low concentrations of total available chlorine.

Commercial assay systems are available for assaying hemodialysis units for available chlorine. One assay utilizes tablets or dry powder, and another utilizes dry chemistry test strips. Each assay has advantages and disadvantages, and neither assay satisfies the different testing requirements needed for a hemodialysis unit.

The tablet method has good sensitivity (e.g., 0.1 ppm) and is less expensive per assay. However, the tablet method is more cumbersome to perform and requires more technician time. The dry chemistry test strips usually are not as sensitive as the tablet method and can cost more per test. Nevertheless, the strip test is very easy and convenient, particularly when operating a mobile hemodialysis unit. In most hemodialysis centers, the test strip is used as a screening test for residual chlorine, whereas the tablet method is used for more critical water testing. Because of the differences in test requirements, most hemodialysis centers are forced to stock both the tablet and dry chemistry test systems.

Dialysis facilities rely on the tablet method using a liquid chemistry assay procedure for the determination of low concentrations of total available chlorine in water. In the assay, chloramine is allowed to react with iodide ion to form iodine, which in turn reacts with N,N-diethyl-p-phenylenediamine (DPD) indicator to generate a light pink color. The sensitivity of the test is achieved by increasing the depth of view through a long verticle path of the reaction tube. As previously stated, the test is cumbersome and time consuming. Conversion of this test method to a strip format is difficult because such a long depth of view is not feasible.

HI SENSE REAGENT STRIP, marketed by Serim Research Corporation, Elkhart, Ind., is another commercially available chloramine test device. In the test, chloramine first is reacted with an iodide ion solution to form iodine, which in turn reacts with a leuco dye impregnated on a membrane. The test requires multiple operation steps and about approximately eight (8) minutes to complete. The test provides only qualitative results by showing positive or negative with no color. The test lacks quantitative information on the chloramine level and also lacks the convenience of a single step test and short reaction time of 60 seconds or less, which are essential for a rapid routine assay.

In the parent application, now U.S. Pat. No. 5,811,254, a single assay for assaying both the high and the low available chlorine concentration range was disclosed. That disclosure showed that it was possible to cross the 10,000 fold difference in chlorine concentration between a working sanitizing solution and a residual chlorine concentration, and detect and differentiate concentration levels over a broad range. Using the test strips makes it difficult to detect ultralow levels of chlorine, i.e., below 0.1 ppm. As opposed to the dip-and-read, it now was found that by repeatedly exposing the strip to the test sample, the strip can detect lower levels of chlorine. Yet, sensitivity still is limited because the process also causes rinsing of the indicator from the strip, thereby making the color on the reagent pad barely visible. Furthermore, the iodide ion in the test pad also is quickly rinsed from the test pad to such a low concentration that catalytic conversion of chloramine by iodide became very slow. This makes the prior test strip less reliable for low-level total chlorine testing.

In order to overcome these problems, it is necessary to immobilize the indicator on the substrate matrix to prevent it from being rinsed off the test pad, and the iodide ions must be anchored in such a way that they are slowly released during the test. The present disclosure sets forth a practical, approach to solving these problems. In particular, the present invention is directed to providing an assay for total available chlorine that is capable of quantitatively measuring total available chlorine concentration over the range of 0 to about 2 ppm, and especially about 0.05 to about 1.50 ppm.

The present invention, therefore, is directed to an assay method and device that can be used to assay for total available chlorine, both free and bound available chlorine, present at 2 ppm or less. Accordingly, a test strip can be used to test for residual chlorine in the rinse water after cleaning the hemodialysis unit or for the chlorine content of the source water for the dialyzer. As illustrated hereafter, the present test strips have a good sensitivity and a detection range over 0 to about 2 ppm total available chlorine with a continuous color response. Such a determination provides important information with respect to whether potentially harmful amounts of available chlorine are present in rinse water or dialysis water.

The present method of assaying for total available chlorine in an aqueous test sample yields trustworthy and reproducible results by utilizing an indicator reagent composition that undergoes a color transition in response to a low concentration of total available chlorine, and not as a result of a competing chemical or physical interaction, such as a preferential interaction with another test sample component. For example, the present indicator reagent composition has sufficient sensitivity to quantitatively detect 0.1 ppm or less total available chlorine.

In accordance with the present invention, an indicator reagent composition can be incorporated into a carrier matrix to provide sufficient sensitivity and color differentiation to assay for total available chlorine concentration over the range of 0 ppm to about 2 ppm, and typically about 0.05 to about 1.50 ppm. In addition, although dry phase test strips have been used to assay for chlorine concentration, no dry phase test strip has been used to quantitatively assay for total available chlorine over such a low concentration range. Examples of prior disclosures relating to assaying for chlorine include Storm U.S. Pat. No. 3,718,605; Reiss U.S. Pat. No. 4,938,926; Ross, Jr. et al. U.S. Pat. No. 4,049,382; Frant U.S. Pat. No. 5,300,442, Harp U.S. Pat. No. 5,362,650; O'Brien et al. U.S. Pat. No. 4,904,605; and J. D. Johnson et al., *Analytical Chemistry*, 40(13), pages 1744–1750 (1969).

SUMMARY OF THE INVENTION

In brief, the present invention is directed to a new and improved composition, test device, and method of determining the total available chlorine concentration of a test sample. A device includes a test pad comprising a suitable carrier matrix incorporating an indicator reagent composition capable of converting combined available chlorine to free available chlorine, and interacting with free available chlorine to produce a detectable response to total available chlorine concentration. A carrier matrix of the test pad comprises a bibulous material, such as filter paper; a nonbibulous material, such as a strip, layer, or membrane of a polymerized material; or a mixture thereof. An indicator reagent composition is homogeneously incorporated into the carrier matrix, and the carrier matrix then holds the indicator reagent composition homogeneously throughout the carrier matrix while maintaining carrier matrix penetrability by the test sample.

More particularly, the present invention is directed to a method of assaying for the total available chlorine content of aqueous test samples by utilizing a new indicator reagent composition. It has been demonstrated that a reagent composition including: (a) an indicator capable of interacting with free available chlorine to provide a detectable and measurable response, (b) a buffer, like a polycarboxylic acid, (c) an optional surfactant, like an anionic surfactant, (d) a catalyst, (e) a polymer, and (f) a catalytic amount of iodide ion or a peroxidase enzyme, affords sufficient sensitivity to test sample total available chlorine content, and a sufficient color differentiation between test samples of different total available chlorine content over the range of 0 to about 2 ppm, and particularly 0.05 to about 1.50 ppm. In accordance with an important feature of the present invention, the indicator reagent composition has a pH of about 4 to about 6.

An accurate and reliable quantitative determination for total available chlorine in a test sample is achieved because the indicator reagent composition is maintained at a pH of about 4 to about 6, and contains an iodide ion or peroxidase catalyst. By utilizing an indicator reagent composition of the present invention, the quantitative assay for total available chlorine in liquid test samples is more sensitive and accurate because the combined available chlorine in the test sample is quickly converted to free available chlorine. The indicator reagent composition then is able to detect the total available chlorine present in the test sample.

Therefore, a buffer is included in the indicator reagent composition to maintain a pH of about 4 to about 6 and achieve a more accurate measurement of the total available chlorine concentration of the test sample. The buffer is included in the indicator reagent composition to maintain the reagent composition within a pH range wherein the combined available chlorine, i.e., chloramine, is quickly converted to free available chlorine. The presence of a catalytic amount of iodide ion or a peroxidase enzyme further facilitates, and speeds, conversion of combined available chlorine to free available chlorine.

Therefore, one aspect of the present invention is to provide a method and composition for quantitatively determining a low concentration of total available chlorine concentration of an aqueous liquid. The composition converts the combined available chlorine to free available chlorine, and interacts with the free available chlorine to produce a change in color of a test device that is indicative of the total available chlorine concentration of the test sample.

Another aspect of the present invention is to provide a method of assaying aqueous test samples, said method having sufficient sensitivity and sufficient visual color resolution to allow differentiation between, and the quantitative measurement of, test samples having different low total available chlorine concentrations.

Yet another object of the present invention is to provide a sensitive method of assaying test samples for total available chlorine concentration over the range of 0 to about 2 ppm total available chlorine. Accordingly, the present method is able to detect residual chlorine present in rinse water, i.e., less than 0.5 ppm, or in source water for a dialysis unit, i.e., less than 0.1 ppm.

Another aspect of the present invention is to provide an indicator reagent composition that interacts with free available chlorine and undergoes a visually or instrumentally differentiable color transition to allow a determination of total available chlorine concentration of a test sample.

Another aspect of the present invention is to provide a method of assaying for the total available chlorine content of a liquid test sample by incorporating an indicator reagent composition into a dry phase detection device, wherein the indicator reagent composition comprises: (a) an indicator capable of interacting with free available chlorine to provide a detectable and measurable response, (b) a buffer, (c) an optional surfactant, (d) a catalyst, (e) a polymer, and (f) a suitable carrier, and wherein the indicator reagent composition has a pH of about 4 to about 6.

Still another aspect of the present invention is to provide a new and improved method of assaying for a low total available chlorine concentration of an aqueous test sample by utilizing a test device, including a carrier matrix, said carrier matrix comprising a bibulous matrix, like filter paper, or a nonbibulous matrix, like a glass fiber or a layer of a permeable polymeric material, and said carrier matrix having incorporated therein an indicator reagent composition capable of converting bound available chlorine to free available chlorine, and of interacting with free available chlorine present in the test sample, to provide a color transition that can be correlated to the total available chlorine concentration of the test sample.

A further aspect of the present invention is to provide an improved dry phase test strip that incorporates an indicator reagent composition comprising a suitable indicator, a buffer, an optional surfactant, a catalyst, and a polymer, and having a pH of about 4 to about 6, into the carrier matrix, and thereby provide a quantitative assay for the total available chlorine content of a test sample.

The above and other aspects and advantages and novel features of the present invention will become apparent from the following detailed description of the preferred embodiments.

DETAILED DESCRIPTION OF THE PREFERRED EMBODIMENTS

In accordance with the method of the present invention, a quantitative assay of aqueous test samples for a low concentration of total available chlorine is accomplished by utilizing an indicator reagent composition that includes (a) an indicator capable of interacting with free available chlorine to provide a detectable and measurable response, (b) a buffer, (c) an optional surfactant, (d) a catalyst, and (e) a polymer. By employing an indicator reagent composition of the present invention, having a pH of about 4 to about 6, sufficient sensitivity and sufficient visual color differentiation between test samples of different total available chlorine content is achieved. In accordance with the method of the present invention, test samples having a total available chlorine content of 0 to about 2 ppm, and particularly 0.05 to about 1.50 ppm, can be measured and differentiated.

To achieve the full advantage of the present invention, the method and composition are employed in dry phase, test pad assays to determine the total available chlorine concentration of aqueous test samples. A dry phase test strip, including a test pad comprising a carrier matrix incorporating an indicator reagent composition of the present invention, allows the rapid quantitative assay of test samples by visual means.

In particular, the present invention allows determination of the total available chlorine concentration of a test sample by the visual color change of a test pad on a test strip resulting from contact between the test strip and the test sample. Total available chlorine concentration of the test sample is determined by correlating the detected free available chlorine concentration to the total available chlorine concentration of the test sample. The test strip includes a test pad comprising an inert carrier matrix incorporating an indicator reagent composition. The present composition and method allow the rapid calorimetric determination of the total available chlorine concentration of a test sample by quickly converting the bound available chlorine to free available chlorine, and assaying for the resulting total free chlorine concentration. Previous assay methods employed compositions that avoided measurement of bound available chlorine. In contrast, the present method measures the total available chlorine content, i.e., free and bound available chlorine, by utilizing a composition having a pH of about 4 to about 6, and which contains a catalyst to increase the rate of conversion of combined available chlorine to free available chlorine.

An important component of the present indicator reagent composition is the indicator. The indicator included in the indicator reagent composition is limited only in that the indicator is capable of undergoing a detectable response, and preferably a chromogenic response, in the presence of free available chlorine. Accordingly, the indicator preferably is a redox indicator that undergoes a color transition, or other detectable response, upon conversion from its reduced state to its oxidized state by free available chlorine. The indicator dye should be sufficiently stable such that free available chlorine is present before a color transition occurs. To achieve the full advantage of the present invention, the indicator dye undergoes a color transition through various detectable and measurable degrees and intensities of color such that the degree and intensity of the color transition can be correlated to the concentration of total available chlorine in a test sample.

It should be noted that the indicator is incapable of interacting with bound available chlorine. Therefore, as explained in detail hereafter, the bound available chlorine is converted to free available chlorine. The indicator, therefore, responds to the total available chlorine concentration of the test sample.

The indicator, therefore, typically is a redox indicator. Preferred redox indicators are the benzidine-type indicators, i.e., benzidine and benzidine derivatives. The benzidine-type indicators have the ability to develop easily detectable and differentiable color hues of varying intensity, which makes these indicators useful in quantitative assays. Although the exact mechanism of color formation by benzidine-type indicators in the presence of various analytes is not known, it is known that two sequential color forms occur: a first colored species which is blue in color, and a second colored species, which is brown. The blue color species tends to be transient and changes to the brown color species. Therefore, it has been necessary to detect a color change within a prescribed time period or to stabilize the blue color. Otherwise, the significance of the color transition, i.e., correlation to analyte concentration, is lost because subtle shades of blue, which are easily distinguishable, yield to the less easily differentiated brown hues.

Benzidine-type indicators have the structure:

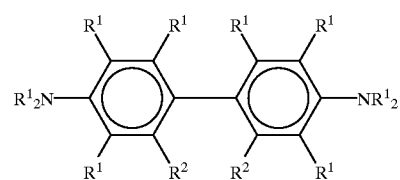

wherein the $R^1$ and $R^2$ substituents, same or different, can be hydrogen, lower alkyl (i.e., alkyl having 1 to about 6 carbon atoms), lower alkyloxy (i.e., alkyloxy having 1 to about 6 carbon atoms), amino, aryl, or aryloxy. Moreover, the $R^2$ substituents together can form $-(CH_2)_n-$, wherein n is 1 or 2. In addition to the above, the $R^1$ and $R^2$ groups can be substituted such as with hydroxy, halogen, cyano, and similar substituents. Typical benzidine-type indicators include, but are not limited to, benzidine, o-tolidine, o-dianisidine, 2,7-diamino-fluorene, 3,3',5,5'-tetramethylbenzidine (hereafter tetramethylbenzidine or TMB), 3,3'-diaminobenzidine, 3,3',5,5'-tetra(alkyl)benzidine, the various N- and N'-substituted benzidines and others, and mixtures thereof.

Another useful class of dyes are the heterocyclic azine indicators, for example, bis(N-ethylquinol-2-one)azine and (N-methylbenzthiozal-2-one) (1-ethyl-3-phenyl-5- methyltriazol-2-one)azine. Preferably, the indicator is a benzidine-type indicator. To achieve the full advantage of the present invention, the indicator is 3,3',5,5'-tetramethylbenzidine.

The indicator typically is present in the indicator reagent composition in a concentration of about 1 to about 200 mM, and preferably in a concentration of about 10 to about 150 mM. The amount of indicator in the indicator reagent composition can be less than about 1 mM, or greater than about 200 mM, depending upon the intensity of the color transition that a particular indicator undergoes upon oxidation. In general, the amount of indicator included in the indicator reagent composition is limited only in that the indicator undergoes a detectable color transition in proportion to the concentration of free available chlorine. The detection of free available chlorine then can be correlated to total available chlorine content of the test sample.

As discussed in detail hereafter, a preferred method of assaying for a low concentration of total available chlorine involves repeatedly contacting the test pad with the test sample, e.g., applying a stream of test sample to the test pad. This method has a tendency to rinse the indicator from the test pad, and thereby adversely affect assay results. In accordance with an important feature of the present invention, the indicator is immobilized on the carrier matrix by a covalent chemical bond, or, preferably, by physical encapsulation or entrapment within the polymer. Immobilization of the indicator will be discussed in detail hereafter.

In addition to the indicator, the indicator reagent composition also contains a buffer. In accordance with an important feature of the present invention, the buffer buffers the indicator reagent composition in the range of about 4 to about 6, and preferably about 4.5 to about 5.5. To achieve the full advantage of present invention, the buffer maintains the composition at a pH of about 4.8 to about 5.3. In the pH range of about 4 to about 6, the bound available chlorine, i.e., chloramine, is converted to free available chlorine at a sufficient rate such that the bound available chlorine is assayed and detected by the present indicator reagent composition.

A pH of about 4 to about 6, therefore, provides an indicator reagent composition having a very high sensitivity to chlorine. Free available chlorine interacts with an indicator over a wide pH range. However, bound available chlorine cannot interact with the indicator above pH about 6. The interaction between bound available chlorine and the indicator increases significantly at pH about 5.5 or less, and especially at pH 5 or less, i.e., bound available chlorine is converted to free available chlorine, which in turn can interact with the indicator. However, below pH about 5, the development of a background color increases. This background color interferes with an accurate assay for total available chlorine. Therefore, to achieve the full advantage of the present invention, the indicator reagent composition is buffered at a pH of about 4.8 to about 5.3.

The identity of the buffer is not particularly limited, as long as the indicator reagent composition is buffered in the range of about 4 to about 6. Therefore, useful buffers include, but are not limited to, polycarboxylic acids, phosphate, borate, acetate, and mixtures thereof. Preferred buffers are polycarboxylic acids, and especially polycarboxylic acids wherein the carboxyl groups are separated by two to five carbon atoms. Examples of useful polycarboxylic acid buffers include, but are not limited to, citric acid, succinic acid, lactic acid, and ketoglutaric acid. As demonstrated in detail hereafter, the polycarboxylic acid buffers improve the color response of the indicator to free available chlorine, and provide a more stable color response. It has been theorized, but is not relied upon herein, that the polycarboxylic acid is capable of complexing with the indicator to form a brighter and more spectacular color, and to stabilize the color. The concentration of buffer in the composition typically is about 20 to about 600 mM, and preferably about 50 to about 200 mM.

In addition to the indicator and the buffer, the indicator reagent composition also contains an optional surfactant. The optional surfactant is an anionic surfactant, a nonionic surfactant, or a mixture thereof. The optional surfactant is present in the indicator reagent composition in an amount of 0% to about 0.02%, and preferably 0% to about 0.01%, by weight of the composition. To achieve the full advantage of the present invention, the surfactant is present in an amount of about 0.001% to about 0.007% by weight of the composition.

As illustrated in detail hereafter, the optional surfactant is present in a minimal amount, if at all. The optional surfactant, if used, is present in a sufficient amount to facilitate wetting of the surface of the polymer, but not in a sufficiently low amount to avoid solubilizing the indicator. The optional surfactant, therefore, assists wetting of the carrier matrix by the test sample, without adversely affecting the color transition of the indicator in response to free available chlorine. As further illustrated hereafter, the optional surfactant may assist the present indicator reagent composition assay for a low concentration of total available chlorine, i.e., 0 ppm to about 2 ppm.

With respect to effectively wetting the polymer surface, the surfactant can be an anionic surfactant, a nonionic surfactant, or a mixture thereof. Each of these classes of surfactants effectively wets the surface of the polymer. Anionic and cationic surfactants also improve the stability of the color transition of the indicator. Cationic surfactants and zwitterionic surfactants, as demonstrated hereafter, did not stabilize the color transition.

The optional surfactant has an HLB (hydrophilic-lipophilic balance) of less than 50, and preferably less than 20. To achieve the full advantage of the present invention, the optional surfactant has an HLB value of about 4 to about 20.

Useful nonionic surfactants include, but are not limited to, an ethoxylated polysorbate, e.g., polysorbate 20 through polysorbate 85, an ethoxylated alcohol, e.g., a $C_{10}$ to $C_{22}$ alcohol ethoxylated with about 10 to about 25 moles of ethylene oxide, an ethoxylated phenol, i.e., an ethoxylated octylphenol, nonylphenol, or dodecylphenol with about 8 to about 30 moles of ethylene oxide, a polyethylene glycol, e.g., PEG-8 through PEG-40, a polypropylene glycol, e.g., PPG-9 through PPG-34, an ethylene glycol-propylene glycol copolymer, e.g., a poloxamer, a polybutylene glycol, and similar non-ionic surfactants, and mixtures thereof. In general, a useful nonionic surfactant has an HLB value of about 4 to less than 50.

Anionic surfactants useful in the present invention are not particularly limited. Usually, the anionic surfactant includes a hydrophobic moiety, such as a carbon chain including about eight carbon atoms to about 30 carbon atoms, and particularly about twelve carbon atoms to about twenty carbon atoms; and further includes a hydrophilic moiety, such as sulfate, sulfonate, carbonate, phosphate, or carboxylate. Often, the hydrophobic carbon chain is etherified, such as with ethylene oxide or propylene oxide, to impart a particular physical property or reduced surface tension, to the anionic surfactant.

The anionic surfactants are well known, and can be a fatty acid, a salt of a fatty acid, an ethoxylated fatty acid, or a salt of an ethoxylated fatty acid, for example. Therefore, suitable anionic surfactants include, but are not limited to, compounds in the classes known as alkyl sulfates, alkyl ether sulfates, alkyl ether sulfonates, sulfate esters of an alkylphenoxy polyoxyethylene ethanol, alpha-olefin sulfonates, beta-alkyloxy alkane sulfonates, alkyl arylsulfonates, alkyl carbonates, alkyl ether carboxylates, fatty acids, sulfosuccinates, alkyl ether sulfosuccinates, sarcosinates, octoxynol phosphates, nonoxynol phosphates, taurates, fatty taurides, sulfated monoglycerides, fatty acid amido polyoxyethylene sulfates, and isothienates; or mixtures thereof. Many additional anionic surfactants are described in *McCutcheon's, Detergents and Emulsifiers*, 1993 *Annual*, published by McCutcheon Division, MC Publishing Co., and incorporated herein by reference.

Usually, the anionic surfactant is present in the composition as a neutralized salt in the form of a sodium, potassium, lithium, ammonium, alkyl-ammonium, or hydroxyalkylammonium salt, wherein the alkyl moiety includes one to about three carbon atoms. The alkyl sulfates and alkyl ether sulfates are particularly effective classes of anionic surfactants. Consequently, exemplary anionic surfactants useful in the composition and method of the present invention include, but are not limited to, the ammonium, monoethanolamine, diethanolamine, triethanolamine, isopropylamine, sodium, potassium, lithium, or magnesium salt of lauryl sulfate, dodecylbenzenesulfonate, lauryl sulfosuccinate, lauryl ether sulfate, lauryl ether carboxylate, lauryl sarcosinate, cocomethyl tauride, and sulfosuccinate half ester amide, or mixtures thereof. Examples of especially useful anionic surfactants are a lauryl sulfate salt, a lauryl ether sulfate salt, a lauryl phosphate, a sulfosuccinate salt, a dodecylsulfonate salt, a cholate salt, a $C_8$ to $C_{18}$ fatty acid, and mixtures thereof.

In addition to the indicator, buffer, and optional surfactant, the indicator reagent composition also contains about 100 to about 1500 ppm of a catalyst to increase the rate at which the indicator reagent composition converts the combined available chlorine to free available chlorine, thereby making it possible to assay for the amount of combined and free, i.e., total, available chlorine in the test sample. Preferably, the indicator reagent composition contains about 200 to about 1200 ppm of a catalyst, and, to achieve the full advantage of the present invention, about 500 to about 1000 ppm. At these concentrations, the catalyst does not interfere with the color transition of the indicator, or cause a false positive assay.

Tests showed that a combination of an indicator with a low level of catalyst was as an effective test system for total available chlorine. However, accelerating the catalytic reaction by increasing the concentration of catalyst showed that high level of catalyst, like iodide ion, interferes with the color transition of the indicator. This interference was much more pronounced at a higher chlorine level, e.g., 5 ppm or higher. It was also surprisingly found that for a total chlorine concentration of less than 1.0 ppm, and particularly less than 0.1 ppm, a high catalyst concentration does not interfere with the color transition of the indicator. This discovery allows the use of a higher catalyst concentration to accelerate this reaction, and thus makes the rapid detection of an ultralow level of total available chlorine possible.

In one embodiment, the catalyst is a peroxidase, like horseradish peroxidase. The peroxidase reduces the interference of ammonium ions in the total available chlorine assay. It is important to reduce ammonium ion interference because ammonium ions react with free available chlorine to form a chloramine, and thereby convert free available chlorine to bound available chlorine. The presence of a peroxidase reverses this reaction, and frees the bound available chlorine from chloramine such that the resulting free available chlorine is available for assay by a present indicator reagent composition.

The finding that a peroxidase stabilizes and enhances color formation in a total available chlorine assay is both new and unexpected. It was expected that a peroxidase, which is a protein, would interfere in the reaction between free available chlorine and the indicator. This interference is expected because free available chlorine reacts with nitrogen present in a protein to form a chloramine, which binds chlorine and makes it unavailable for reaction with the indicator. Surprisingly, however, it was found that incorporating a catalytic amount of a peroxidase into a present indicator reagent composition does not interfere with the reaction between the indicator and free available chlorine and thereby reduce test strip sensitivity, but, to the contrary, increases the sensitivity of the test strips and yields an accurate quantitative assay for total available chlorine.

In particular, the effect of incorporating horseradish peroxidase is illustrated below. Free available chlorine reacts with variety of redox indicators, the most common of which are benzidine indicators, such as orthotolidine or 3,3',5,5'-tetramethylbenzidine. An important problem associated with such indicators is that they exhibit a very narrow sensitivity range for chlorine, i.e., there is no variation of test strip color when chlorine level is 10 ppm or higher. Therefore, it is impossible to visually quantify a chlorine level greater than about 10 ppm. However, by adding horseradish peroxidase to an indicator reagent composition, the test strip color varies over the range 0 ppm to about 2 ppm total available chlorine with a differentiable color transition from colorless to sky blue.

In another test, it was found that peroxidase increases the rate of conversion of combined available chlorine to free available chlorine. It was found that a test strip incorporating an indicator reagent composition lacking peroxidase reacted very slowly with a test sample containing 1 ppm of chloramine. However, when peroxidase was incorporated into the composition, a test strip reacted with 1 ppm of chloramine in 45 seconds to generate a color transition identical to 1 ppm of free available chlorine.

Incorporating a peroxidase into an indicator reagent composition provides another advantage. In particular, when peroxidase is present, the test strip can be used to assay for peroxide in addition to total available chlorine. Hydrogen peroxide is a commonly used disinfectant for hemodialysis units, but most indicator reagent compositions are insensitive to peroxide unless a catalytic peroxidase enzyme is present.

Accordingly, a present test strip can be used to assay for peroxide over the range of 0 to greater than about 10 ppm. This capability greatly increases versatility of the present test strips because medical workers often use hydrogen peroxide to sanitize hemodialysis units. The present test strips, therefore, can be used by medical personnel as the sole test strip to assay for residual sanitizing compounds in the rinse water of a hemo-dialysis unit, regardless of whether the sanitizer is chlorine or a peroxide. Medical laboratories and clinics, therefore, do not have to stock different types of assay kits for testing low total available chlorine and peroxide. Similar to testing for low, residual amounts of chlorine, the present test strips turn blue upon contact with a test sample containing residual peroxide. A single test strip, therefore, provides the convenience of a dual test system for hydrogen peroxide and total available chlorine.

In another embodiment, the catalyst is iodide ion, typically in the form of an alkali metal iodide, like lithium iodide, sodium iodide, or, preferably, potassium iodide. The amount of iodide ion present in the indicator reagent composition is about 100 to about 1500 ppm, and preferably about 250 to about 1000 ppm. To achieve the full advantage of the present invention, the amount of iodide ion present in the composition is about 350 to about 800 ppm. It has been determined that one part of iodide ion can react with at least four equivalents of chloramine, thereby increasing the rate of conversion of bound available chlorine to a detectable free chlorine species.

Iodide ion allows an indirect assay of the bound available chlorine. In particular, the catalytic mechanism involves recycling of iodide ion and iodine. The iodide ion first is oxidized by chloramine to iodine, which in turn oxidizes an indicator, like tetramethylbenzidine (TMB), to an oxidized, colored indicator complex. As a result, iodine is reduced back to iodide ion which then repeats the oxidation-reduction cycle until all of the chloramine substrate is consumed. Like any catalytic reaction, the rate of this conversion is proportional to the level of catalyst. At a potassium iodide concentration of the present invention, completion of the reaction is almost instantaneous.

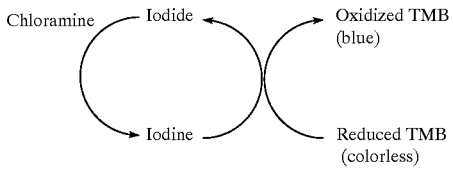

In accordance with an important feature of the present invention, the amount of iodide ion can be maintained at a high level, and, at the same time, not interfere with the assay for total available chlorine. If the amount of available iodide ion is too high, iodine can be formed too rapidly and precipitated before the iodine can react with the indicator. As a consequence, the intensity of color transition is reduced, and a low assay results. At the same time, the yellow/brown color of iodine causes strip color to shift to a dirty green hue, making color differentiation to correlate the color transition to total available chlorine concentration more difficult.

However, release of iodide ion can be controlled by entrapping the iodide ions in a polymer which forms a relatively hard gel, which provides a slow release of iodide ion into solution. As discussed hereafter, the polymer preferably is sufficiently hydrophilic to allow wetting by the aqueous test sample, and forms a gel structure which is not readily soluble in water.

Therefore, a polymer also is incorporated into the indicator reagent composition. The polymer retards the release of iodide ion, and improves the stability and uniformity of the color transition of the test device. The polymer also helps incorporate the indicator reagent composition uniformly throughout the carrier matrix. Suitable polymers include, but are not limited to, polyvinylpyrrolidone, polyvinyl alcohol, gum arabic, gelatin, algin, carrageenan, casein, albumin, methyl cellulose, and similar natural and synthetic polymeric materials. Preferred polymers are gelatin and cellulose-type polymers.

Specific examples of natural, cellulose-type polymers are hydroxypropylcellulose, hydroxyethylcellulose, hydroxybutylcellulose, and sodium carboxymethylcellulose. A useful synthetic polymer is a polyvinylpyrrolidone of average molecular weight about 40,000 and available commercially from ISP Corp., Wayne, N.J. A polymer generally is included in the indicator reagent composition in an amount of about 0.05% to about 4%, and preferably from about 0.2% to about 3%, by total weight of the indicator reagent composition.

The natural, cellulose-type polymers and gelatin are preferred over synthetic polymers, like polyvinylpyrrolidone, because the synthetic polymers have a tendency to impart a green hue to the test strip. The cellulose-type polymers impart a preferred bluish color. The polymers also serve a thickening function to help facilitate impregnation of the carrier matrix with the indicator reagent composition.

The presence of a polymer in an indicator reagent composition also enhances chloramine reactivity. The effectiveness of a polymer with respect to enhancing chloramine reactivity is directly related to the hydrophobicity of the polymer. For example, GANTREZ ES 225 (an ethyl ester of a PVM/MA copolymer), KLUCEL (hydroxypropylcellulose), and PVP K60 (polyvinylpyrrolidone) have a decreasing effectiveness with respect to enhancing chloramine reactivity, and also have a decreasing hydrophobicity. Test strips impregnated with an indicator reagent composition containing GANTREZ ES 225 were essentially 100% reactive with chloramine, but also tended to develop background color with chlorine-free water. PVP K60 generated little background color, but is only 50% reactive with chloramine. KLUCEL provided the best overall results when considering both chloramine reactivity and lack of background color. In particular, when using KLUCEL, the test strip had an 80% to 90% chloramine reactivity and no background color.

The above-mentioned chloramine reactivities were evaluated by comparing the color of a test strip after immersion into hypochlorite (free chlorine) solutions either containing or free of ammonium sulfate. The addition of ammonium ions to the hypochlorite solution converts hypochlorite to chloramine, which consequently is unreactive to free chlorine test strips. Test strip reactivity to chloramine can be improved and restored to 100% by various approaches described herein, including a pH of about 4 to 6, the presence of a surfactant, the presence of a catalyst, and the presence of a polymer. The percent reactivity was visually estimated by comparing the intensity of test strip color with chloramine in relationship to the equivalent test strip color with free chlorine.

Importantly, the polymer also prevents the indicator from premature rinsing from the test pad during the assay. As discussed hereafter, the preferred method of assaying for a low total available chlorine concentration is to apply a stream of the test sample to the test strip. This method has a tendency to extract and rinse the indicator from the test strip.

Therefore, the indicator can be immobilized on the carrier matrix by physical encapsulation or entrapment within the polymer. Entrapment within the polymer is facilitated by incorporating a hydrophobic indicator that is soluble in organic solvent in a polymer having hydrophobic properties. Particularly useful polymers are GANTREZ ES 225, GANTREZ ES 325, or a cellulose-type polymer. GANTREZ ES 225 and ES 325 are hydrophobic polymers, and also provide a dried polymer surface having sufficient surface activity to allow coating over, or impregnation with, a second aqueous solution. A cellulose-type polymer, on the other hand, is a hydrophilic polymer, but also has sufficient hydrophobicity and solubility in organic solvents. Both types of polymers entrap the indicator into the polymer matrix when the polymer and indicator are both dissolved in a single solution, and the solution is applied to the carrier matrix. Particularly useful polymers are cellulose-type polymers having hydroxypropyl groups. An additional advantage of the cellulose-type polymers is that these polymers precipitate from solution at an elevated temperature, and form microparticles. These microparticles increase the surface area of the carrier matrix and, as described later, enhance test strip reactivity.

In addition, if necessary or if desired, inert background dyes can be included in the reagent composition to improve the color resolution and differentiation of the color transition in the present assay for total available chlorine. Suitable background dyes include, but are not limited to, ethyl orange (4-(4-diethylaminophenylazo)-benzenesulfonic acid); Orange G (4-(2-hydroxy-(7,9 sodium disulfonate)-1-naphthylazo)-benzene); disperse orange 11, 13, or 25; calcomine orange; methyl orange; and orange II (4-(2-hydroxy-1-naphthylazo) benzenesulfonic acid), or mixtures thereof. A background dye is included in an indicator reagent composition of the present invention in a concentration of 0 mM to about 2 mM, and preferably 0 mM to about 1 mM.

The carrier for the ingredients of an indicator reagent composition includes water. However, because of the limited water solubility of particular ingredients included in the indicator reagent composition, organic solvents, such as acetone, methanol, ethanol, isopropyl alcohol, ethylene glycol, propylene glycol, dimethylformamide, dimethylsulfoxide, acetonitrile, ethyl acetate, and similar solvents can be included in the carrier vehicle. The selection of a suitable organic solvent or solvents, in addition to water, to include in the carrier of the indicator reagent composition is within the capability of those skilled in the art of designing diagnostic assays.

The amount of organic solvent present in an indicator reagent composition generally is 0% to about 90%, and preferably about 10% to about 70%, by weight of the carrier. A carrier comprising water and an organic solvent, like methanol, ethanol, or acetone, is especially preferred because a carrier matrix impregnated with the indicator reagent composition can be dried within a few to several minutes.

As previously described, an indicator reagent composition undergoes a color transition upon contact with a test sample to provide an assay for total available chlorine concentration from the intensity and degree of the color transition. In accordance with an important feature of the present invention, an indicator reagent composition of the present invention provides a sufficiently resolved and differentiated color transition such that the total available chlorine in a test sample can be measured and accurately determined without the use of color-measuring instruments, such as spectrophotometers or calorimeters, over a concentration range of 0 to about 2 ppm. However, if desired, such color-measuring instruments can be used to measure the difference in color degree and intensity between the test sample and a solution having a known concentration of total available chlorine.

The intensity and degree of the color transition are used to determine the total available chlorine content of the test sample by comparing or correlating the color produced by the test sample to colors produced by solutions having a known total available chlorine concentration. In accordance with an important feature of the present invention, the indicator reagent composition provides a sufficiently resolved and differentiated color transition such that the total available chlorine of the test sample can be measured for test samples having a total available chlorine content of 0 to about 2 ppm without the use of color-measuring instruments.

An indicator reagent composition of the present invention, as described above, is used in dry phase, test pad assays for total available chlorine. The dry phase, test pad assay for total available chlorine utilizing a present indicator reagent composition is performed in accordance with methods well known in the art. In general, the assay for total available chlorine is performed by contacting the test sample with an analyte detection device that includes an indicator reagent composition. The analyte detection device can be dipped into the test sample, or the test sample can be applied to the analyte detection device dropwise. Preferably, a stream of the test sample is applied to the analyte detection device. The resulting change in color of the analyte detection device reveals the total available chlorine concentration of the test sample; and, if so designed, the resulting color transition can be compared to a standardized color chart to provide a measurement of the total available chlorine concentration of the test sample.

Typically, the analyte detection device is a test strip impregnated with an indicator reagent composition, designed either as a single pad test strip (to assay only for a single analyte) or as a multiple pad test strip (to assay for several analytes simultaneously). For either type of test strip, the test strip includes a support strip, or handle, normally constructed from a hydrophobic plastic, and a reagent test pad, comprising a bibulous or nonbibulous carrier matrix. In general, the carrier matrix is an absorbent material that allows the test sample to move in response to capillary forces through the matrix to contact the indicator reagent composition and produce a detectable and measurable color transition.

The carrier matrix can be any substance capable of incorporating the chemical reagents required to perform the assay of interest, as long as the carrier matrix is substantially inert with respect to the chemical reagents. The carrier matrix also is porous or absorbent relative to the liquid test sample.

The expression "carrier matrix" refers either to bibulous or nonbibulous matrices that are insoluble in the carrier of the indicator reagent composition and other physiological fluids and that maintain their structural integrity when exposed to the carrier and other physiological fluids. Suitable bibulous matrices include filter paper, sponge materials, cellulose, wood, woven and nonwoven fabrics, and the like. Nonbibulous matrices include glass fiber, polymeric films, and microporous membranes. Other suitable carrier matrices include hydrophilic inorganic powders, such as silica gel, alumina, diatomaceous earth and the like; argillaceous substances; cloth; hydrophilic natural polymeric materials, particularly cellulosic material, like cellulose beads, and especially fiber-containing papers such as filter paper or chromatographic paper; synthetic or modified naturally occurring polymers, such as cellulose acetate, polyvinyl chloride ride, polyacrylamide, polyacrylates, polyurethanes, crosslinked dextran, agarose, and other such crosslinked and noncrosslinked water-insoluble hydrophilic polymers. The carrier matrix can be of different chemical compositions or a mixture of chemical compositions. The matrix also can vary in regards to smoothness and roughness combined with hardness and softness. The handle usually is formed from hydrophobic materials such as cellulose acetate, polyethylene terephthalate, polycarbonate, or polystyrene, and the carrier matrix is most advantageously constructed from filter paper or polymeric films.

The carrier matrix of the test strip can be any bibulous or nonbibulous material that allows permeation by the test sample to saturate the test pad of the test strip that is impregnated with the indicator reagent composition. A preferred carrier matrix is a hydrophilic, bibulous matrix, including cellulosic materials, such as paper, and preferably filter paper. The carrier matrix also can be a hydrophilic, nonbibulous matrix, including polymeric films, such as a polyurethane or a crosslinked gelatin. Such polymeric films possess all of the qualities required of a carrier matrix of the present invention, including suspending and positioning both the essential ingredients and any optional ingredients included in the indicator reagent composition, and permeability of the test sample through the carrier matrix.

The sensitivity of a present test pad is related to the surface area of the carrier matrix. The greater the surface area of the carrier matrix, the higher the intensity of the color transition. This in turn allows differentiation between color transitions resulting from test samples having different low total available chlorine concentrations. Cellulose fiber, in addition to its high porosity, is a preferred carrier matrix for providing a large surface area for the indicator reagent composition. Microfilament synthetic cloth can also be used as the carrier matrix. When a synthetic film is used as the carrier matrix, the addition of fine particles in the coating solution provides additional surface area. The most common particulate materials are microcrystalline cellulose, diatomite, and talc.

In accordance with the method of the present invention, to perform a dry phase test strip assay for total available chlorine, an acetone solution, including: (a) about 1 to about 200 mM of an indicator, such as tetramethylbenzidene; (b) about 0% to about 0.02% by weight of a surfactant, like a sulfosuccinate; (c) about 0.05% to about 4% by weight of a polymer, like a hydrophobic polymer; and (d) any other desired optional ingredients, or solvents, first is prepared. A nonbibulous matrix, such as a polyurethane film, or a bibulous matrix, such as filter paper, then is saturated or impregnated with the acetone solution by immersing or by spraying the acetone solution onto sheets or precut strips or pads of the polyurethane film or filter paper.

Then, after removing the acetone solvent by drying in a forced air oven at a temperature of about 40° C. to about 100° C. for about 2 minutes to about 5 minutes, the polyurethane film or filter paper is saturated and impregnated with an aqueous solution, including: (a) about 20 to about 600 mM of a buffer, like a citrate buffer; (b) about 150 to about 1500 ppm of a catalyst, like a peroxidase or iodide ion; (c) 0% to about 4% by weight of a polymer; and (d) any other desired optional ingredients or solvents, like background dyes, either by immersion or by spraying. After a second oven drying at about 40° C. to about 100° C. for approximately 2 minutes to 15 minutes, the twice-saturated or twice-impregnated polyurethane film or filter paper, if necessary, is cut to an appropriate size, such as a pad having dimensions of about 0.2 in. (inch) (0.5 cm) by about 0.5 in (1.3 cm) to about 0.5 in. (1.3 cm) by about 1 in. (2.5 cm).

It should be understood that it is well within the experimental techniques of those skilled in the art of preparing test devices to determine the proper balance between size of the test pad, the strength of indicator reagent composition solutions, the amount of test sample, and the method of introducing the test sample to the test strip, such as by pipetting rather than dipping, in order to design a quantitative assay for total available chlorine utilizing the method and composition of the present invention.

The dried, twice-impregnated polyurethane film or filter paper then is secured to an opaque or transparent hydrophobic plastic handle with double-sided adhesive tape. The resulting test strip then is contacted with a test sample for a sufficient time to saturate the test pad with the sample. After waiting a predetermined time, such as from about 1 second to about 120 seconds, the test strip is examined, either visually or by instrument, for a response. The color transition, if any, of the test pad reveals the concentration of total available chlorine in the test sample.

In many cases, simple visual observation of the test strip provides the desired information. If more accurate information is required, a color chart bearing color spots corresponding to various known concentrations of total available chlorine can be prepared for the particular indicator reagent composition used in the test strip. The resulting color of the test strip after contact with the test sample then can be compared with the color spots on the chart to determine the concentration of total available chlorine in the test sample. If a still more accurate determination is required, a spectrophotometer or calorimeter can be used to more precisely determine the degree of the color transition. In addition, the dry phase test strip assay can be made quantitative by employing spectrophotometric or calorimetric techniques, as opposed to visual techniques, in order to more reliably and more accurately measure the degree of color transition, and, therefore, more accurately measure the concentration of total available chlorine in the test sample.

In accordance with one embodiment of the present invention, the following dry phase test strips were prepared to perform a dry phase assay for total available chlorine. A strip, a pad, or a sheet of a carrier matrix, like filter paper, first was immersed into an acetone solution including:

| Indicator Reagent Composition Formulation #1 First Immersion Solution | |
| --- | --- |
| Ingredient | Amount |
| Acetone | 40 g |
| TMB[1] | 0.5 g |
| 10% KLUCEL[2] | 5 g |
| Surfactant[3] | 0.002 g |

[1]tetramethylbenzidine indicator;
[2]a 10% aqueous solution of hydroxypropylcellulose, KLUCEL is available from Aqualon Co., Wilmington, DE; and
[3]AEROSOL OT, dioctyl sodium sulfosuccinate, available from Cytec Industries, West Paterson, NJ.

Excess solution was removed from the surface of the filter paper with a scraper bar.

The once-saturated or impregnated filter paper then was dried in a forced air oven having a temperature of about 45° C. to about 80° C. for about 5 minutes. After drying, the once-saturated or impregnated filter paper then was immersed into an aqueous solution including:

| Second Immersion Solution | |
| --- | --- |
| Ingredient | Amount |
| Water | 30 g |
| Citrate Buffer (1M) (pH 5.1) | 3 g |
| Peroxidase | 30 mg |
| 2.5% NATROSOL[4] | 1.5 g |
| 2% BENECEL[5] | 3 g |
| Potassium Iodide | 37 mg |

[4]a 2.5% aqueous solution of hydroxyethylcellulose, NATROSOL is available from Aqualon Co.; and
[5]a 2% aqueous solution of hydroxyethylmethylcellulose, BENECEL is available from Aqualon Co.

The twice-saturated or impregnated filter paper then was dried in an oven having a temperature of about 40° C. to about 80° C. for about 5 minutes. The dried and twice-saturated or impregnated filter paper then was backed with a double-sided adhesive, and slit into 0.2 inch (0.5 cm) wide ribbons. A ribbon of filter paper incorporating an indicator reagent composition of the present invention then is attached to a polystyrene plastic support by means of the double-sided adhesive. The plastic support, including the saturated or impregnated filter paper, then is slit into 0.2 inch (0.5 cm) wide strips. Accordingly, the plastic support includes a pad having dimensions of about 0.2 inch (0.5 cm) by about 0.2 inch (0.5 cm) of saturated or impregnated filter paper to provide a test pad comprising a filter paper carrier matrix incorporating an indicator reagent composition of the present invention.

In addition, it should be understood that an indicator reagent composition of the present invention demonstrates sufficient stability such that the carrier matrix can be saturated or impregnated by immersing the carrier matrix into a single aqueous solution, or a single aqueous acetone solution, including all of the essential and optional ingredients of the indicator reagent composition. However, the two-step method utilizing two immersions is preferred because certain indicator reagent composition ingredients have relatively low water solubilities, and a more stable color transition is observed.

To demonstrate the new and unexpected results achieved by the method of the present invention, dry phase test strips incorporating an indicator reagent composition of the present invention (Formulation #1) were used to assay standardized solutions containing available chlorine. Individual test strips were dipped into a series of standardized solutions, containing from 0 ppm to 1.26 ppm available chlorine. The standardized solutions contained chloramine, and were prepared by diluting a 5.25% (by weight) sodium hypochlorite solution with deionized water, and adding four equivalents of ammonium sulfate to the dilution hypochlorite solution.

The standardized solutions were assayed for total available chlorine by applying a continuous stream of a standardized solution onto the test pad for about sixty (60) seconds. The color of the test strips then was observed. Timing of the strip reaction is not critical. However, for consistency, the strip color was evaluated after 10 seconds after application of the standardized solution. It should be noted that the present test strips can detect 0.1 ppm or less total available chlorine by contacting the test strip with the test sample for 60 seconds. Any trace of a blue color is considered a positive test for available chlorine. The test results are set forth in Table 1.

TABLE 1

Test Strip Reactivity

| Chloramine Concentration (ppm) | Strip Readings (Relative Color Scale) | Strip Color[6] |
|---|---|---|
| 0 | 0 | Off White |
| 0.07 | <0.1 | |
| 0.10 | 0.1 | Misty Blue |
| 0.23 | >0.1 | |
| 0.35 | <0.5 | |
| 0.48 | 0.5 | Aqua Blue |
| 0.70 | >0.5 | |
| 0.82 | <1.0 | |
| 1.01 | 1.0 | Sky Blue |
| 1.26 | >1.0 | |

[6]test strip was colorless prior to immersion into the standardized solution.

The results set forth in Table 1 show that a test strip of the present invention is capable of assaying for total available chlorine over the entire range of 0 to about 2 ppm by providing a differentiable color response over this entire range. Accordingly, a single test strip can be used to ensure that a source water for a dialysis unit has an available chlorine concentration below 0.1 ppm, and that the residual chlorine in rinse water from a dialysis unit, after sanitizing, is below toxic levels.

In particular, Table 1 shows that if the test strip shows any degree of blue color, then the rinse water contains a potentially toxic amount of total available chlorine, and, therefore, rinsing of the hemodialysis unit with deionized water should be continued. Similarly, if that same test strip is blue as a result of assaying a source water, then the source water for use in a hemodialysis unit contains a potentially toxic amount of total available chlorine. The results in Table 1 also show that in the low concentration range (e.g., about 2 ppm or less) color differentiation between different total available chlorine concentrations is relatively easy to distinguish.

To demonstrate the effect of a surfactant, solutions containing different surfactants were individually impregnated onto filter paper, such as Schleicher & Schuell 903. The solutions contained the following ingredients, wherein the identity of the surfactant was varied:

| | |
|---|---|
| Acetone | 5 g |
| Tetramethylbenzidene | 0.5 g |
| Surfactant | 0.005 g. |

Filter paper was dipped in a solution, then dried at 65° C. for 5 minutes. The dried filter papers were made into strips by cutting into 0.2 inch squares, which were adhered to a plastic handle using double-side adhesive tape. The resulting test strips were dipped into solutions having different free available chlorine concentrations. The color of each test strip was visually observed and recorded. Table 2 summarizes the test results using different surfactants.

TABLE 2

Effect of Surfactant on Assay Range Using Tetramethylbenzidine

| Dilution Factor[7] | 1:10 | 1:50 | 1:500 | 1:5000 | 1:10,000 |
|---|---|---|---|---|---|
| Nonionic Surfactants[8] | | | | | |
| BRIJ 35 | Y[12] | Y | Y/Gr | Bl | Lt/Blue |
| TWEEN 20 | Y | Y | Y/Gr | Bl | Lt/Blue |
| TRITON X-100 | Y | Y | Y/Gr | Bl | Lt/Blue |
| Anionic Surfactants[9] | | | | | |
| DBS | Br | Bk/Bl | Bl | Bl | Lt/Blue |
| SDS | Br | Bk/Bl | Bl | Bl | Lt/Blue |
| DOSS | Br | Gr/Bl | Bl | Bl | Lt/Blue |
| Cholate | Br | Br | Bl | Bl | Lt/Blue |
| Benzoic acid[10] | Br | Bk/Bl | Bl | Bl | Lt/Blue |
| Lauric acid | Br | Bk/Bl | Bl | Bl | Lt/Blue |
| Caprylic acid | Br | Bk/Bl | Bl | Bl | Lt/Blue |
| Cationic Surfactants[11] | | | | | |
| CTAB | Y | Y | Gr | Gr | Gr |
| CPC | Y | Y | Y | Bl | Lt/Blue |
| Zwitterionic Surfactants[11] | | | | | |
| Z-08 | Y | Y | Gr | Bl | Lt/Blue |
| CHAPS | Y | Y | Gr | Gr | Lt/Blue |
| Control | | | | | |
| None | Y | Y | Gr | Gr | Lt/Blue |

TABLE 2-continued

Effect of Surfactant on Assay Range Using Tetramethylbenzidine

| Dilution Factor[7] | 1:10 | 1:50 | 1:500 | 1:5000 | 1:10,000 |
| --- | --- | --- | --- | --- | --- |

[7]diluting 1 volume part of aqueous 5.25% (by weight) sodium hypochlorite solution with indicated parts of water;
[8]BRIJ 35--polyethylene glycol dodecyl ether (23 moles ethylene oxide), TWEEN 20--polyethylene glycol sorbitan monolaurate (20 moles ethylene oxide), and TRITON X-100--polyethylene glycol tert-octyl phenyl ether (9 moles ethylene oxide);
[9]DBS--dodecylbenzene sulfonate, SDS--sodium dodecylsulfate, DOSS--dioctyl sulfosuccininate, and cholate--sodium salt of cholic acid;
[10]benzoic acid is not a surfactant, but is capable of stabilizing color formation;
[11]CTAB--cetyltrimethylammonium chloride, CPC--cetylpyridinum chloride, Z-08--Zwittergent 3-08, and CHAPS--3, [(3-cholamidopropyl)-dimethylammonio]-1-propane sulfonate; and
[12]color designations: Y--yellow; Br--brown; Bk--black; Dk--dark; Gr--green; Bl--blue; Y/Gr--yellowish green; Bk/Bl--black blue; Dk/Bl--dark blue, Lt/Bl--light blue.

As illustrated in Table 2, anionic surfactants have an excellent ability to prevent oxidized tetramethylbenzidine, that is blue in color, from being further oxidized and turning brown in color. The class of anionic surfactant present in an indicator reagent composition is not important, e.g, sulfate, sulfonate, carboxylate, phosphate, and similar hydrophilic moieties are useful. However, the hydrophobic moiety of the anionic surfactant can have an effect. The tests show that a linear hydrophobic moiety, alone or with phenyl groups, is slightly more effective in stabilizing the color of the indicator than a bulkier hydrophobic moiety, such as cholate or dioctyl sulfosuccinate. It is theorized that both the hydrophilic group, and the hydrophobic moiety of the surfactant interact with the indicator, thereby protecting the indicator from further oxidation, and further color change. Nonionic surfactants also were effective in stabilizing the color transition, but cationic and zwitterionic surfactants failed to effectively prevent further oxidation of an oxidized indicator.

As previously stated, the indicator reagent composition is buffered in a pH range of about 4 to about 6. It also has been found that the identity of the buffer has an effect with respect to stabilizing the color transition and preventing the colored, oxidized form of the indicator from being further oxidized and turning the test strip brown. In particular, a citrate buffer and a phosphate buffer were equally effective with respect to stabilizing the color transition of a TMB indicator in the presence of free available chlorine, although the color of a test strip containing a citrate buffer has a brighter and cleaner blue color than a test strip containing a phosphate buffer. The following Table 3 illustrates the effect of different buffers on color stability of an indicator reagent composition using TMB as the indicator.

TABLE 3

Effect of Buffer on Color Stability

| Dilution Factor[6] | 1:10 | 1:50 | 1:500 | 1:5000 | 1:10,000 |
| --- | --- | --- | --- | --- | --- |
| Buffer (pH) | | | | | |
| Citrate (5.1) | Br[12] | Bk/Bl | Bl | Bl | Lt/Bl |
| Succinate (5.2) | Br | Bk/Bl | Bl | Bl | Lt/Bl |
| 2-Ketoglutarate (5.6) | Br | Br | Bl | Bl | Lt/Bl |
| Lactate (5.1) | Br | Dk/Bl | Bl | Bl | Lt/Bl |
| Phosphate (5.3) | Br | Bk/Bl | Bl | Bl | Lt/Bl |
| Borate (5.4) | Y | Y | Gr | Lt/Bl | Lt/Bl |

In addition, the ability of a peroxidase to stabilize the color transition of a test strip and catalyze the assay for total available chlorine was demonstrated by adding 50 milligrams of horseradish peroxidase to the second immersion solution of Formulation #1, preparing test strips, and using the test strips to assay for total available chlorine of solutions containing chloramine. The tests showed that peroxidase increased the reaction rate to convert bound chlorine to free chlorine, and the test strip underwent a complete color transition faster than a test strip lacking peroxidase.

From the visual assays and the data presented in Tables 1-3, it has been demonstrated that a particularly useful indicator is tetramethylbenzidine. An indicator reagent composition of the present invention that includes tetramethylbenzidine, in addition to a surfactant and a buffer to buffer the composition to a pH of about 4 to about 6, exhibits a sufficiently dramatic color transition, from light blue to brown, to provide a sensitive and accurate assay for total available chlorine in a test sample. The color transition also is sufficiently resolvable and differentiable, either visually or by instrument, such that an unknown concentration of total available chlorine in a test sample can be determined. Furthermore, it has been found that the indicator is stabilized by interaction with a surfactant, and that a catalyst can convert bound available chlorine to free available chlorine, such that the color transition endpoint is reached within about 1 second to about 2 minutes.

In accordance with an important feature of the present invention, the continuing and substantial problems in dry phase test strips for assaying a low concentration of total available chlorine, including the instability of the indicator, are essentially eliminated by the present invention. An indicator reagent composition of the present invention provides a differentiable response to total available chlorine over the concentration range of 0 to about 2 ppm of the test sample. Therefore, accurate and reliable assays for total available chlorine in test samples can be performed by utilizing an indicator reagent composition and device of the present invention.

Obviously, many modifications and variations of the invention as hereinbefore set forth can be made without departing from the spirit and scope thereof, and, therefore, only such limitations should be imposed as are indicated by the appended claims.

What is claimed is:

1. A composition capable of exhibiting a detectable and measurable color transition in response to a total available chlorine concentration of 0 to about 2 ppm, said composition comprising:

(a) an indicator capable of interacting with free available chlorine;

(b) a buffer;

(c) 0% to about 0.02%, by weight of the composition, of a nonionic surfactant, an anionic surfactant, or a mixture thereof;

(d) about 150 to about 1500 ppm of a catalyst selected from the group consisting of a peroxidase enzyme, iodide ion, and mixtures thereof;

(e) about 0.05% to about 4%, by weight of the composition, of a polymer; and (f) a carrier comprising water, wherein the composition has a pH of about 4 to about 6.

2. The composition of claim 1 wherein the indicator is present in a concentration of about 1 to about 200 millimoles per liter of the composition.

3. The composition of claim 1 wherein the indicator comprises a redox indicator, a heterocyclic azine indicator, or a mixture thereof.

4. The composition of claim 1 wherein the indicator is a benzidine-type indicator having a structure

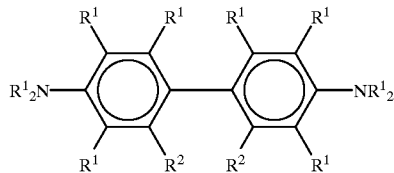

wherein $R^1$ and $R^2$, either the same or different, are selected from the group consisting of hydrogen, a lower alkyl group, a lower alkyloxy group, amino, aryl, and aryloxy, or the $R^2$ substituents can be taken together to form $-(CH_2)_n-$, wherein n is 1 or 2.

5. The composition of claim 4 wherein the indicator is selected from the group consisting of benzidine, o-tolidine, o-dianisidine, 2,7-di-aminofluorene, 3,3',5,5'-tetramethylbenzidine, 3,3'-diaminobenzidine, 3,3',5,5'-tetra(alkyl)benzidine wherein the alkyl group contains two to about six carbon atoms, a nitrogen substituted benzidine, bis(N-ethylquinol-2-one)azine, and (N-methylbenzthiozal-2-one)(1-ethyl-3-phenyl-5-methyltriazol-2-one)azine.

6. The composition of claim 1 wherein the buffer is present in a concentration of about 20 to about 600 millimoles per liter of the composition.

7. The composition of claim 1 wherein the buffer is selected from the group consisting of a polycarboxylic acid wherein the carboxyl groups are separated by two to five carbon atoms, citric acid, succinic acid, ketoglutaric acid, lactic acid, phosphate, borate, acetate, and mixtures thereof.

8. The composition of claim 1 wherein the nonionic surfactant has an HLB value of about 4 to less than 50.

9. The composition of claim 1 wherein the nonionic surfactant is selected from the group consisting of an ethoxylated polysorbate, an ethoxylated alcohol, an ethoxylated phenol, a polyethylene glycol, a polypropylene glycol, an ethylene glycol-propylene glycol copolymer, a polybutylene glycol, and mixtures thereof.

10. The composition of claim 1 wherein the anionic surfactant comprises a sulfate, a sulfonate, a carbonate, a phosphate, or a carboxylate.

11. The composition of claim 1 wherein the anionic surfactant is selected from the group consisting of an alkyl sulfate, an alkyl ether sulfate, an alkyl ether sulfonate, a sulfate ester of an alkylphenoxy polyoxyethylene ethanol, an alpha-olefin sulfonate, a beta-alkyloxy alkane sulfonate, an alkyl arylsulfonate, an alkyl carbonate, an alkyl ether carboxylate, a fatty acid, a sulfosuccinate, an alkyl ether sulfosuccinate, a sarcosinate, an octoxynol phosphate, a taurate, a fatty tauride, a sulfated monoglyceride, a fatty acid amido polyoxyethylene sulfate, and mixtures thereof.

12. The composition of claim 1 wherein the anionic surfactant comprises an ammonium, monoethanolamine, diethanolamine, triethanolamine, isopropylamine, sodium, potassium, lithium, or magnesium salt of lauryl sulfate, dodecylbenzenesulfonate, lauryl sulfosuccinate, a lauryl ether sulfate, a lauryl ether carboxylate, lauryl sarcosinate, cocomethyl tauride, and a sulfosuccinate half ester amide, and mixtures thereof.

13. The composition of claim 1 wherein the polymer is selected from the group consisting of polyvinylpyrrolidone, polyvinyl alcohol, gum arabic, gelatin, algin, carrageenan, casein, albumin, methyl cellulose, hydroxypropylcellulose, hydroxyethyl-cellulose, hydroxybutylcellulose, sodium carboxy-methylcellulose, and mixture thereof.

14. The composition of claim 1 wherein the polymer is hydrophobic.

15. The composition of claim 1 wherein the carrier comprises 0% to about 90% by weight of the carrier of an organic solvent.

16. The composition of claim 1 having a pH of about 4.5 to about 5.5.

17. The composition of claim 1 having a pH of about 4.8 to about 5.3.

18. A method of determining total available chlorine content of an aqueous test sample containing 0 to about 2 ppm total available chlorine, said method comprising:
    (a) contacting the aqueous test sample with an indicator reagent composition comprising:
        (i) an indicator capable of interacting with free available chlorine;
        (ii) a buffer;
        (iii) 0% to about 0.02%, by weight of the composition, of a nonionic surfactant, an anionic surfactant, or a mixture thereof;
        (iv) about 150 to about 1500 ppm of a catalyst selected from the group consisting of a peroxidase enzyme, iodide ion, and mixtures thereof;
        (v) about 0.05% to about 4%, by weight of the composition, of a polymer; and
        (vi) a carrier comprising water, wherein the composition has a pH of about 4 to about 6;
    (b) determining the total available chloride content of the aqueous test sample from the intensity and degree of the color transition are determine visually or instrumentally.

19. The method of claim 18 wherein the aqueous test sample has a total available chlorine content of about 0.05 to about 1.50 ppm.

20. A method of determining the total available chlorine content of an aqueous sample containing 0 to about 2 ppm total available chlorine, said method comprising:
    (a) contacting the aqueous sample with an analyte detection device comprising a test pad, said test pad having incorporated therein an indicator reagent composition comprising:
        (i) an indicator capable of interacting with free available chlorine;
        (ii) a buffer;
        (iii) 0% to about 0.02%, by weight of the composition, of a nonionic surfactant, an anionic surfactant, or a mixture thereof;
        (iv) about 150 to about 1500 ppm of a catalyst selected from the group consisting of a peroxidase enzyme, iodide ion, and mixtures thereof;
        (v) about 0.05% to about 4%, by weight of the composition, of a polymer; and
        (vi) a carrier comprising water, wherein the composition has a pH of about 4 to about 6;
    (b) determining the total available chlorine content of the aqueous sample from the intensity and degree of a color transition of the indicator reagent composition.

21. The method of claim 20 wherein the aqueous test sample contacts the analyte detection device by directing a stream of the aqueous test sample onto the test pad.

22. A method of determining the total available chlorine content of an aqueous sample having a total available chlorine content of 0 to about 2 ppm comprising:
 (a) contacting the aqueous sample with an analyte detection device comprising a test pad having incorporated therein:
  (i) an indicator capable of interacting with free available chlorine;
  (ii) a buffer;
  (iii) 0% to about 0.02%, by weight of the composition, of a nonionic surfactant, an anionic surfactant, or a mixture thereof;
  (iv) about 150 to about 1500 ppm of a catalyst selected from the group consisting of a peroxidase enzyme, iodide ion, and mixtures thereof;
  (v) about 0.05% to about 4%, by weight of the composition, of a polymer; and
  (vi) a carrier comprising water, wherein the composition has a pH of about 4 to about 6;
 (b) examining the analyte detection device for a color transition; and
 (c) correlating the color transition to the total available chlorine content of the aqueous sample.

23. An analyte-detection device to determine the total available chlorine content of an aqueous test sample comprising:
 a support strip;
 a test pad; and
 an indicator reagent composition incorporated into the test paid, said reagent composition comprising:
  (a) an indicator capable of interacting with free available chlorine;
  (b) a buffer;
  (c) 0% to about 0.02%, by weight of the composition, of a nonionic surfactant, an anionic surfactant, or a mixture thereof;
  (d) about 150 to about 1500 ppm of a catalyst selected from the group consisting of a peroxidase enzyme, iodide ion, and mixtures thereof;
  (e) about 0.05% to about 4%, by weight of the composition, of a polymer;
 wherein the composition has a pH of about 4.8 to about 5.3.

* * * * *